United States Patent [19]

Dervan et al.

[11] Patent Number: 4,795,700

[45] Date of Patent: Jan. 3, 1989

[54] NUCLEIC ACID PROBES AND METHODS OF USING SAME

[75] Inventors: Peter B. Dervan; Geoffrey B. Dreyer, both of Pasadena, Calif.

[73] Assignee: California Institute of Technology, Pasadena, Calif.

[21] Appl. No.: 695,082

[22] Filed: Jan. 25, 1985

[51] Int. Cl.[4] .......................... C12Q 1/70; C12Q 1/68; C07H 21/00
[52] U.S. Cl. ............................................. 435/5; 435/6; 435/29; 435/91; 436/811; 935/78; 536/27
[58] Field of Search .................... 436/501, 811; 435/6, 435/5, 29, 91; 935/78; 536/27

[56] References Cited

U.S. PATENT DOCUMENTS

| | | | |
|---|---|---|---|
| 4,358,535 | 11/1982 | Falkow et al. | 435/38 X |
| 4,563,417 | 1/1986 | Albarella et al. | 935/77 X |
| 4,599,303 | 7/1986 | Yabusaki et al. | 935/77 X |
| 4,665,184 | 5/1987 | Dervan et al. | 530/331 X |

OTHER PUBLICATIONS

Hertzberg, R. P. et al, *J. Am. Chem. Soc.*, vol. 104, 1982, pp. 313–315.
Schultz, P. G. et al, *Proc. Natl. Acad. Sci. USA*, vol. 80, 1983, pp. 6834–6837.
Taylor, J. S. et al, *Tetrahedron*, vol. 40, No. 3, 1984, pp. 457–465.
Van Dyke, M. M. et al, *Science*, vol. 225, 1984, pp. 1122–1127.
Chu, B. C. F. et al, *Proc. Natl. Acad. Sci. USA*, vol. 82, 1985, pp. 963–967.
Dreyer, G. B. et al, *Proc. Natl. Acad. Sci. USA*, vol. 82, 1985, pp. 968–972.

*Primary Examiner*—Charles F. Warren
*Assistant Examiner*—Jeremy M. Jay
*Attorney, Agent, or Firm*—Lyon & Lyon

[57] ABSTRACT

A probe and method for specific recognition or cleavage of single-stranded DNA or RNA at desired loci utilizing sequence-specific polynucleotide-chelator probes. The probe may also be utilized as a diagnostic agent when the metal ion is replaced with a radiolabelled, fluorescing, or otherwise detectable metal.

39 Claims, 4 Drawing Sheets

3'-TCAAATAGTGTCAATTTAACGATTGCGTCAGTCCGTGGCACATACTTTAGATTGTTAC-5'

5'-TAACGCAGTCAGGCACCGT-3'

FIG. 4.

NUCLEIC ACID PROBES AND METHODS OF USING SAME

FIELD OF THE INVENTION

This invention relates to nucleic acid probes and to methods of using such probes for diagnostic and therapeutic purposes.

BACKGROUND OF THE INVENTION

A new era in medical sciences has been generated by the remarkable advances made in the field of genetic engineering. The genetic engineering revolution has been hastened by the discovery of naturally occurring enzymes which cleave double helical deoxyribonucleic acid (hereafter DNA) molecules. These enzymes, called restriction endonucleases, cleave DNA molecules at very specific recognition sites within the DNA polymer. The recognition sites are specific sequences of nucleotides for each restriction enzyme. The sequence-specific cleavage of DNA has found many applications such as DNA sequence determinations, chromosome analyses, gene isolation and recombinant DNA mainipulations. Other applications include new and useful diagnostic reagents to detect pathogens and aberrant DNA molecules.

The usefulness of restriction endonucleases has been limited to cleavage of double-stranded DNA molecules containing the nucleic acid sequences recognized by the limited number of these enzymes. In addition, DNA cleavage by restriction endonucleases is limited to the cleavage of DNA at loci where the sequence recognition site occurs. Thus, endonucleases cannot be used to specifically excise a particular piece of DNA unless, by chance, that piece of DNA contains specific nucleic acid sequences recognized by the limited number of known endonucleases.

The development of synthetic reagents for the sequence-specific modification of DNA provides additional tools useful in research, diagnostics and chemotherapeutic strategies. For example, the attachment of a DNA-cleaving moiety such as ethylenediaminetetraacetic acid-iron complex, (hereafter EDTA-Fe(II)), to a DNA binding molecule produces an efficient DNA cleaving molecule as described by Hertzbert & Dervan, *J. Am. Chem. Soc.* 104, p. 313–315 (1982); *Biochemistry* 23, p. 3934–3945 (1984). Methidiumpropyl-EDTA (hereafter MPE), which contains the metal chelator EDTA tethered to the DNA intercalator methidium, has been shown to cleave double helical DNA efficiently in a reaction dependent on ferrous ion (FeII) and dioxygen ($O_2$). Addition of reducing agents such as dithiothreitol (hereafter DTT) increases the efficiency of DNA cleavage, as reported by Hertzberg & Dervan, *J. Am. Chem. Soc.* 104, p. 313–315 (1982); *Biochemistry* 23 p. 3934–3945 (1984). MPE-Fe(II) cleaves DNA in a relatively nonsequence specific manner and with significantly lower sequence specificity than the enzyme DNAse I and is thus useful as a research tool in "footprinting" experiments to identify the binding locations of small molecules such as drugs and proteins on native DNA. Van Dyke & Dervan, *Cold Spring Harbor Symp. Quant. Biol.* 47, p. 347–353 (1982); *Biochemistry* 22 p. 2373–2377 (1983); *Nucleic Acids Res.* 11, p. 5555–5567 (1983); and *Science* 225 p. 1122–1127 (1984).

Many small molecules important in antibiotic, antiviral and antitumor chemotherapy bind to double helical DNA. Until recently knowledge of the DNA base sequence specificities for these small DNA-binding molecules, such as antibiotics, was limited due to the need to rely on the overall binding affinity of such drugs to homopolymer and copolymer DNAs. The attachment of the cleaving complex EDTA-Fe(II) to antibiotics such as distamycin (hereafter DE) followed by DNA cleavage pattern analyses from Maxam-Gilbert sequencing gels has yielded information on the DNA binding sites and orientation of such drugs on DNA. Hertzerg and Dervan, *J. Am. Chem. Soc.*, 104, p. 313–315 (1982); Taylor et al., *Tetrahedron* 40, p. 457–465 (1984); *Science*, 225, p. 1122–1127 (1984).

The mechanism of cleavage by EDTA-FeII complexed with synthetic molecules such as methidium or antibiotics such as distamycin is thought to occur by a common mechanism wherein MPE or DE bind in the minor groove of the right-handed DNA helix by hydropobic and hydrogen binding interactions. Cleavage most likely involves diffusible hydroxyl radical. Hertzberg and Dervan, *Biochemistry* 23, p. 3934–3945 (1984); *Tetrahedron*, 40, pg. 457–465 (1984).

Nucleic acid hybridization probes consisting of sequences of deoxyribonucleotides (DNA) or ribonucleotides (RNA) are well-known in the art. Typically, to construct a probe, selected target DNA is obtained as a single strand and copies of a portion of the strand are synthesized in the laboratory and labelled using radioactive isotopes, fluorescing molecules or enzymes that react with a substrate to produce a color change. When exposed to complementary strands of target DNA, for example in a sample of tissue fluid taken from a patient, the labelled DNA probe binds to (hybridizes) its complementary DNA sequence. The label on the probe is then detected and the DNA of interest is thus located. The probe may also be used to target RNA sequences. Finally, probes constructed of RNA sequences may be used to hybridize with a single complementary strand of double-helical DNA forming heteroduplexes without necessitating denaturation of the double-helical DNA. Thomas, et al., *Proc. Nat. Acad. Sci.* 73, p. 2294–2298 (1976); Casey and Davidson, *Nucl. Acids Res.*, 4, p. 1539–1552 (1977). DNA probes are proving useful in locating and identifying selected genes, and in the diagnosis and treatment of infection, genetic disorders and cancer. See, U.S. Pat. No. 4,358,535.

The above described methods for sequence-specific DNA cleavage have been limited to double-stranded DNA and to those sequences of DNA recognized by antibiotics and DNA intercalators such as methidium. It would provide increased specificity and flexibility with regard to the possible target nucleic acid sequences if sequence-specific cleavage of single stranded nucleic acid (DNA and RNA) and a wider variety of nucleic acid sequences could be accomplished.

Accordingly, it is an object of this invention to provide a method for preparing novel polynucleotide-chelator probes for recognizing specific nucleic acid sequences.

It is another object of this invention to provide a method for using polynucleotide-chelator probes to cleave single-stranded nucleic acid at a specific location.

Yet another object of this invention is to provide a method for using polynucleotide-chelator probes for chemotherapeutic and diagnostic purposes.

Still another object of this invention is to provide polynucleotide-chelator probes containing novel nucleosides functionalized with a metal chelator.

These and other objects and advantages of the invention will be apparent from the detailed description which follows.

SUMMARY OF THE INVENTION

The present invention, which comprises attaching a nucleic acid-cleaving moiety, such as EDTA-Fe(II) to a polynucleotide complementary to and thus capable of binding with a specific nucleic acid sequence, provides a method for specific cleavage of single-stranded (and denatured double-stranded) deoxyribonucleic acid (hereafter DNA) or ribonucleic acid (hereafter RNA) at any desired loci utilizing such sequence-specific compositions as nucleic acid probes. In the preferred embodiment, the nucleic acid-cleaving moiety, a metal chelator, is attached to a nucleoside base during synthesis of a novel nucleoside and the so-modified nucleoside is then incorporated into a selected polynucleotide using standard procedures. This polynucleotide containing the chelator-modified nucleoside is complementary to a nucleotide sequence in the DNA or RNA for which a probe is desired. Alternatively, the metal chelator may be attached to a selected nucleotide located within a polynucleotide sequence. In the presence of dioxygen ($O_2$), an appropriate metal ion and a reducing agent the DNA or RNA-chelator probe affords selective cleavage at its complementary RNA or DNA sequence. The probes of the present invention are not limited to the production of sequence specific cleavage of DNA or RNA but may also be utilized as diagnostic agents when a radiolabelled, fluorescing, or otherwise detectable metal ion is attached to the probe.

BRIEF DESCRIPTION OF THE DRAWINGS

FIG. 4 represents a histogram of a pBR322 DNA cleavage pattern obtained from densitometry of the autoradiogram (from FIG. 3) following incubation with the DNA-EDTA probe in the presence of Fe(II) and DTT.

DETAILED DESCRIPTION OF THE PREFERRED EMBODIMENT

Figure 1:
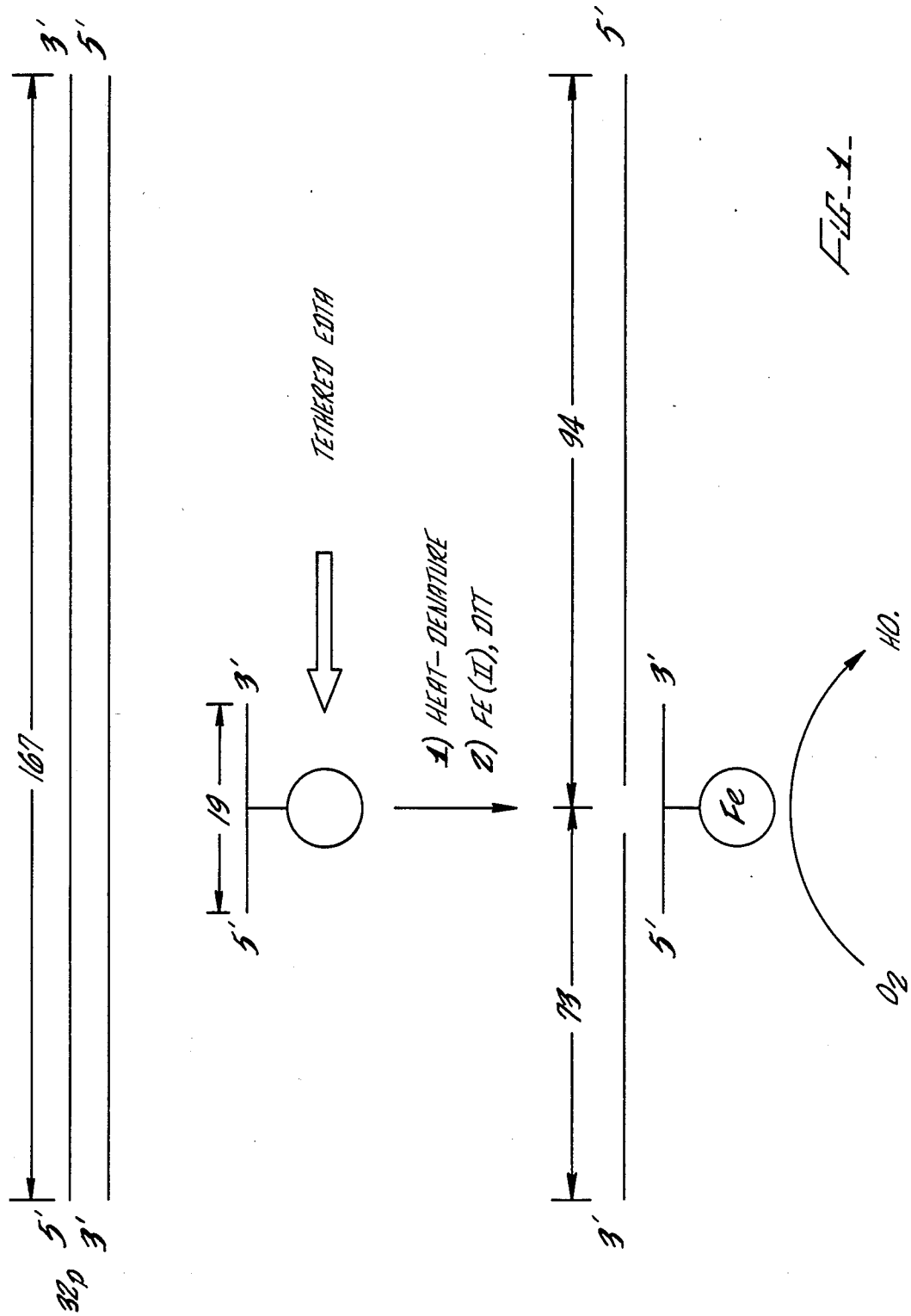
FIG. 1 is a schematic representation of the cleavage of pBR322 DNA by a DNA probe consisting of EDTA-tethered to a 19 bp sequence of DNA complementary to a 19 bp sequence of pBR322 DNA.

The polynucleotide-chelator probes of the present invention for a specific nucleic acid sequence are preferably produced by the incorporation of a novel nucleoside functionalized with a metal chelator such as ethylene-diamine tetraacetic acid (hereafter EDTA). Other polyamino carboxylic metal chelators may be utilized in place of EDTA such as 1,2-diaminocyclohexane tetracetic acid (DCTA), diethylenetriamine pentaacetic acid (DTPA) ethylenediamine di (-o-hydroxyphenylacetic acid) (EDDHA) and hydroxyethylene diamine triaacetic acid (HEEDTA). The metal chelator is attached to the novel nucleotide during synthesis via a hydrocarbon-amide tether which may consist of several carbon atoms.

The specificity of the probe for the reaction site is prescribed by the nucleotide sequence within which the metal chelator is attached. The EDTA-functionalized nucleoside can then be incorporated into polydeoxyribonucleotides (DNA) or polyribonucleotides (RNA) of any desired length and sequenced using routine phosphoramidite or phosphotriester procedures.

For the construction of the polynucleotide-chelator probes, a versatile and practical method compatible with known oligonucleotide synthesis methodology has been developed and is described in detail in the Example which follows. The probes of this invention incorporate a chelator-functionalized nucleoside into the sequence of nucleotides comprising the probe. The methods of the present invention allow the attachment of a metal chelator, such as EDTA, at various positions in the nucleotide sequence depending on the selected nucleoside which is functionalized with the chelator. Nucleosides, such as those derived from the nucleoside bases thymine, uracil, cytosine, adenine and guanine may be functionalized with the chelator. For example, aliphatic substitution of a metal chelator at the fifth carbon of pyrimidine nucleotide bases can be achieved by palladium mediated olefination reactions as described by Bergstrom, & Ruth, *J. Carbohydrates Nucleosides Nucleotides* 4, p. 257-269 (1977); Bergstrom, & Ogawa, *J. Am. Chem. Soc.* 100, p. 8106-8112 (1978); Heck, *J. Am. Chem. Soc.* 90, p. 5518-5526 (1968); and Langer, Waldrop, & Ward, *Proc. Natl. Acad. Sci.* (U.S.A.) 78(11), p. 6633-6637 (1981). Palladium (II) coupling chemistry has been used to introduce alkyl side chains at carbon five of uridine, deoxyuridine, cytosine and deoxycytosine via the carbon five mercury or halogen derivatives. Langer, Waldrop and Ward, *Proc. Nat. Acad. Sci.* 78(11), p. 6633-6637 (1981).

The metal chelator may also be attached at carbon eight of adenosine and guanosine and deoxyadenosine and deoxyguanosine nucleosides and at carbon seven of deazaadenosine and deazaguanosine nucleosides. The purine bases adenine and guanine can be readily halogenated, and mercurated at carbon eight. Mercuration and halogenation also occur readily at carbon seven of 7-deazapurine nucleoside derivatives. Holmes and Robins, *J. Am. Chem. Soc.* 86, p. 1242 (1963). Alkyl side chains could be introduced in these halogen and mercuri derivatives by Palladium II coupling chemistry. Dale, Livingston and Ward, *Proc. Nat. Acad. Sci.* 70, p. 2238-2242 (1973). Direct free-radical alkylation may also be used to introduce alkyl side chains containing a metal chelator at carbon eight of the purine nucleosides. Christenson et. al., *Biochem.* 14(7) p. 1490-1496 (1975).

The metal chelator may also be attached to amino derivatives of nucleosides at the 5' carbon atom of the ribose. Delaney, et. al., *J. Carbohydrates, Nucleosides, Nucleotides*, 8 (5), p. 445-459 (1981). Alternatively, the metal chelator may be attached to hydrocarbon chains at nitrogen four of cytidine and deoxycytidine nucleosides, using bisulfite-catalyzed transamination to introduce a 3-aminopropylside chain at carbon four. Draper and Gold, *Biochem.* 19, p. 1774-1781 (1980). In addition, the metal chelator may be attached at nitrogen four using 4-thiouridine. Smrt, *Neoplasma*, 24, p. 461-466 (1977). A chelator attached to a hydrocarbon tether may also be incorporated at nitrogen six of adenosine and deoxyadenosine, and at nitrogen two of guanosine and deoxyguanosine using reduction amination. Borch, et. al., *J. Am. Chem. Soc.* 93 p. 2897 (1971).

The tethered metal chelator may be attached to the 3' or 5' terminal phosphate of polynucleotides and nucleic acids using a phosphoamidate linkage, (Chu et. al., *Nucl. Acids Res.*, 11, p. 6513-6528 (1983)), or to an internucleotidyl phosphate of polynucleotides. Asseline et al., *C.R. Acad. Sc. Paris*, 297, p. 369-376 (1983); *Proc. Nat. Acad. Sci.* 81, p. 3297-3301 (1984). Finally the chelator could be tethered to uridine 3' phosphate and uridine 5' phosphate 6-aminohexyl esters. Smrt, *Coll. Czech. Chem. Commun.*, 44, p. 589-592 (1979).

Thus, a chelator may be incorporated into the polynucleotide sequences of the probe at various positions for which the chemistry for attachment at such positions is known, provided such attachment is accomplished so as not to disrupt the hydrogen base pair bonding between the DNA or RNA sequences during hybridization of the probes.

In the preferred embodiment disclosed herein in the Example below, the chelator-functionalized nucleoside is incorporated into the polynucleotide sequence of the probe chemically using known oligonucleotide synthesis methodology. Alternatively, enzymatic procedures for incorporating chelator-functionalized nucleosides could be used. The metal chelator may be attached to a phosphate within a nucleoside mono-, di- or triphosphate. In this embodiment, the chelator may be tethered to a phosphate group in a nucleoside triphosphate which is labelled with $p^{32}$. An enzyme, such as the Klenow fragment of DNA polymerase I, may then be used to incorporate the labelled nucleoside bearing the chelator into a poly-deoxyribonucleotide sequence. The end-labelled DNA sequence would form part of a double-stranded DNA fragment which would then be denatured to yield a single-stranded $P^{32}$-end-labelled polynucleotide sequence capable of functioning as a DNA or RNA probe as described in this invention.

In addition to providing sequence-specific cleavage of selected DNA or RNA, the probes of the present invention may be used as iagnostic agents for the detection of the presence of DNA or RNA viruses in biological fluids such as blood or urine or in tissue specimens after standard fixation techniques. DNA and RNA viruses such as Cytomegalovirus, hepatitis virus, or measles virus in biological fluids or tissue specimens may be detected after applying standard techniques for dissolving the viral coats, denaturing the viral genome, if the genome is double-stranded, to prepare single-stranded polynucleotides, and hybridizing the single-stranded viral genome with a probe prepared as disclosed in the present application containing a sequence complementary to at least a part of the viral genome. Capture of the double-stranded hybridization product is accomplished by detection of the hybridized product using means appropriate to the properties of the metal ion used. One would detect a radioactive metal by conventional methods used by those in the art for detecting radioactive emissions or detect fluorescing metals using appropriate wave length detectors. For DNA-EDTA Fe(II) probes one would detect cleavage of the DNA or RNA target strand by gel electrophoresis techniques i.e. the appearance of shorter, discrete nucleic acid fragments.

These polynucleotide-chelator probes may also be used to detect specific DNA sequences (i.e., genes) in tissue specimens. All or part of nucleotide sequences for several oncogenes and several abberrant genes which are associated with specific genetic abnormalities are known. A probe as disclosed in the present application, complementary to at least part of the sequences of an oncogene or an aberrant gene sequence may also be prepared and utilized to detect the presence of these genes in tissue or cell samples. After extraction of the DNA from the specimens by conventional techniques and denaturation procedures to produce single-stranded DNA, one can hybridize the probe prepared as disclosed in the present application and detect the hybridized product by means appropriate to the detection of the metal ion utilized.

Another use for the probes of this invention is for chemotherapy for various abnormalities in a human patient. Thus, the polynucleotide-chelator probes may be used to target messenger RNA sequences which encode proteins which are linked to cancer or other disease proliferation.

The example which follows describes an embodiment wherein a DNA-EDTA probe is synthesized using a novel nucleoside, 5'-DMT-T*-triethylester derived from deoxyuridine and functionalized by the metal chelator EDTA. This nucleoside is described in detail in co-pending application, entitled "CHELATOR-FUNCTIONALIZED NUCLEOSIDES AND NUCLEOTIDES AND METHODS FOR MAKING SAME", assigned to the same assignee as this application, and filed concurrently herewith, which disclosure is incorporated herein by reference. The EDTA-nucleoside composition is then incorporated into a 19 nucleotide base pair (hereafter bp) sequence of DNA complementary to a 19 bp sequence in a 167 bp restriction fragment of DNA from the plasmid pBR322. This DNA-EDTA probe is then used in the presence of the metal ion Fe(II), atmospheric dioxygen and the reducing agent dithiothreitol (hereafter DTT) to afford specific cleavage at its complementary 19 bp complement in the plasmid DNA fragment.

The invention is further illustrated by the following example.

EXAMPLE I

For this example, synthesis of and cleavage by the DNA-EDTA probe was performed using the following procedures and reagents. Thin layer chromotography (TLC) was performed with precoated 0.25 mm Silica Gel 60 F-254 TLC plates (EM Reagents). Flash chromatography was performed with EM Reagents Silica Gel 60 (230-400 mesh). Reagent grade chemicals were used without purification unless otherwise stated. Deoxyuridine and DTT were purchased from Calbiochem. Protected deoxynucleoside phosphoramidites were prepared by procedures as described in the literature. Beaucage, & Caruthers, *Tetrahedron Lett.* 22, p. 1859-1962, (1981). $K_2PdCl_4$, and 10% Pd on C were from Alfa-Ventron. $Fe(NH_4)_26H_2O$ was from Baker. Aqueous 5'-[$\alpha$-$^{32}$P] dATP (3,000 Ci/mmol) was from Amersham, and aqueous 5'-[$\alpha$-$^{32}$P] ATP (7,000 Ci/mmol) was from ICN. Standard NTP's were from Boehringer Mannheim. All enzymes were from New England Biolabs except bacterial alkaline phosphatase and T4 polynucleotide kinase, which were from Bethesda Research Laboratories. Solutions of $Fe(NH,)(SO_4)_2$ and DTT were freshly prepared. Plasmid pBR322 was grown in *E.coli*, strain HB101, and isolated by standard procedures.

Synthesis of the DNA-EDTA probe

Figure 2:
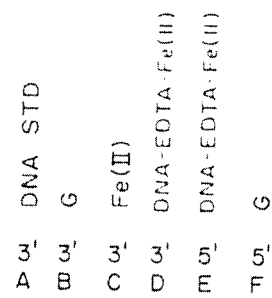
FIG. 2 illustrates the synthesis of the chelator-functionalized nucleoside 5'-DMT-T*-triethylester.

The method of synthesis of the DNA-EDTA probe in this example is based on incorporation of a nucleoside which comprises a protected, EDTA-functionalized derivative of deoxyuridine into a sequence of nucleotides using standard oligonucleotide synthesis procedures to produce a probe 19 nucleotides in length. The synthesis of this novel nucleoside which incorporates the metal chelator EDTA at Carbon-5 of the uracil base is disclosed fully in the co-pending patent application entitled "CHELATOR-FUNCTIONALIZED NUCLEOSIDES AND NUCLEOTIDES AND METHODS OF MAKING SAME". The procedures for synthesis of this nucleoside are incorporated by reference herein and will not be repeated in detail. Briefly, the nucleoside 5'-DMT-T*-triethylester is derived by first modifying 2'-deoxyuridine at the carbon-5 position of the uracil base to yield Nucleoside 3, using a palladium (II)-mediated coupling reaction with methyl acrylate. Nucleoside (3) is then hydrogenated to selectively reduce the exocyclic double bond producing Nucleoside 4. The 5' hydroxyl group of Nucleoside 4 is protected with dimethoxytrityl chloride to give Nucleoside 5. Nucleoside 5 is then reacted with excess ethylenediamine to afford Nucleoside 6, which is coupled directly with the N-hydroxysuccinimide ester of EDTA-triethylester, yielding the nucleoside 5'-DMT-T*-triethylester (FIG. 2).

The synthesis of the 19 nucleotide DNA-EDTA probe containing the nucleoside 5'-DMT-T*-triethylester was accomplished by the manual solid-phase phosphoramidite method using published procedures, beginning with the 5'-DMT-T*-triethylester (4 μmol) bound to a silica support. Dorman, Noble, McBride, & Caruthers *Tetrahedron* 40, p. 95–102 (1984); Adams, Kavka, Wykes, Holder, & Galluppi, *J. Am. Chem. Soc.* 105, p. 661–663 (1983); Matteucci, & Caruthers, *J. Am. Chem. Soc.* 103, p. 3185–3191 (1981), Beaucage & Caruthers *Tetrahedron Lett.* 22 p. 1859–1862 (1981), all of which are incorporated herein by reference. 5'-DMT-T-triethylester was coupled in the tenth addition cycle as follows: 80 mg (79 μmol of nucleoside), was dissolved in CHCl$_3$ (100 μL) and diisopropylethylamine (100 μL), and reacted with chloro-N,N-dimethylaminomethoxyphosphine (20 μL, 160 μmol) under Ar for 4 h. The mixture was dissolved in EtOAc (1 mL), rinsed with saturated aqueous NaCl (×1 mL), dried using Na$_2$SO$_4$ and concentrated. The resulting foam (76 mg) was stored under vacuum (0.2 torr) for 24 h, then was activated with 0.5 M tetrazole in CH$_3$CN (0.6 mL) and coupled (15 min.) to the protected, silica-bound, 5'-detritylated 10-mer CAGGCACCGT. The subsequent DMT cleavage (5% dichloroacetic acid in toluene) was monitored spectrophotometrically which indicated a coupling yield of 97% for 5'DMT-T*-triethylester. The remainder of the oligonucleotide synthesis cycles were as previously described in the following references: Dorman, Noble, McBride, & Caruthers, *Tetrahedron* 40, p. 95–102 (1984); Adams, Kavka, Wykes, Holder, & Galluppi, *J. Am. Chem. Soc.* 105, p. 671–663; Matteucci, & Caruthers, *J. Am. Chem. Soc.* 103, p. 3185–3191 (1981). The penultimate DMT cleavage suggested an overall yield for the 19-nucleotide DNA-EDTA probe of approximately 50%.

Approximately 1/10 of the fully protected, silica-bound 19-nucleotide DNA containing the 5'-DMT-T*-triethylester was shaken with 1:2:2 PhSH:Et$_3$N:dioxane (5.0 mL) for 1 h, rinsed (MeOH), then shaken with 0.1 N NaOH (1.5 mL) for 6 h to clear the DNA from the silica support and to hydrolyze the esters of the EDTA and deprotect the bases. The silica was removed, and showed no color upon treatment with acid, indicating complete detachment of the 19-nucleotide DNA. The supernatant was heated to 50° C. for 13 h, concentrated, treated with HOAc (1.0 mL) for 1.5 h, reconcentrated, and eluted with H$_2$O through Sephadex G10-120.

The crude DNA-EDTA probe obtained above was lyophilized and purified by electrophoresis (450 V, 22 h) on a 2 mm thick 20% polyacrylamide gel using standard procedures. Maxam and Gilbert, *Methods Enz.*, 65, p. 499–560 (1980). The major UV-absorbing band was cut out and eluted with H$_2$O at 60° C. for 24 h, then eluted through Sephadex G10-120, affording 27 nmol (5.8 OD260) of purified 19 nucleotide DNA-EDTA probe. A sample of the purified DNA-EDTA, 5'-endlabeled with T4-kinase and ($\alpha$32p) was homogeneous by electrophoresis on a 20% polyacrylamide gel. The sequence of the probe was confirmed by standard Maxam-Gilbert chemical sequencing methods.

The DNA-EDTA probe nucleotide sequence was 5'-TAACGCAGT*CAGGCACCGT-3' wherein T* denotes the chelator-functionalized nucleoside derived from deoxyuridine which is complementary to a 19-nucleotide sequence in the 167 bp restriction fragment (Eco-RI/Rsa I) from pBR322 plasmid DNA.

Preparation of Labeled Template DNA Fragment

Plasmid pBR322 DNA was digested with Eco RI, then 3-'end labeled with ($\alpha-32p$) dATP using the Klenow fragment of DNA polymerase I by well-known methods. A second enzymatic digest with Rsa I yielded a 3'-end labeled fragment 167 bp in length, containing the 19-nucleotide complement of the DNA-EDTA probe. Sutcliffe, *Cold Spring Harbor Symp. Quant. Biol.* 43, p. 77–90 (1979). This restriction fragment was isolated by polyacrylamide gel electrophoresis. Cleavage of pBR322 with the enzyme Eco RI and successive treatment with the enzymes bacterial alkaline phosphatase, ($\alpha-^{32}P$) ATP and T4-kinase, then Rsa I, yielded the 5'-end labeled 167 bp restriction fragment from the pBR322.

Cleavage of plasmid pBR322 DNA by DNA-EDTA probe

The sequence-specific cleavage of DNA by the DNA-EDTA-Fe(II) probe prepared as described above was examined on a 167 bp 3'-end 32p-labelled Eco RI/Rsa I restriction fragment of DNA from the plasmid pBR322 containing the 19-base complement to the DNA of the probe. The steps of the cleavage procedure are illustrated in FIG. 1. The reaction mixture (8 μL) containing DNA-EDTA probe (0.6 μM), 32P-endcpm), labelled 167 bp template (2,500 cpm), 50 mM Tris (pH 7.4) and 50 mM NaCl, was prepared in 1.5 mL Eppendorf tubes. The reaction mixtures were heated to 95° C. for 3–4 min to denature the template, followed by rapid chilling in ice water to effect hybridization of the probe to te template. The cleavage reactions were initiated by adding aqueous solutions of Fe(II) (1 μL) and DTT (1 μL), such that the final concentrations were 0.5 μM probe, 10 μM Fe(II), and 4 mM DTT. The cleavage reactions were allowed to proceed at 25° C. (pH 7.4) for 60 min, then were terminated by freezing (−78° C.) and lyophilization. These samples were suspended in 4 μL of formamide loading buffer, heat-denatured, and loaded on 0.4 mm-thick, 40 cm-long, 8% polyacrylamide (1:20 crosslinked)/50% urea high-resolution sequencing gels to analyze the cleavage reaction products. Electrophoresis was conducted at 1200 V for 4.5 h. Autoradiography of the gels was carried out at $-50°$ C. on Kodak X-Omat AR film. Copies (20 cm×25 cm) of the original autoradiograms were scanned at 485 nm. The relative peak height for each local maximum was equated with the relative cleavage efficiency.

Figure 3:
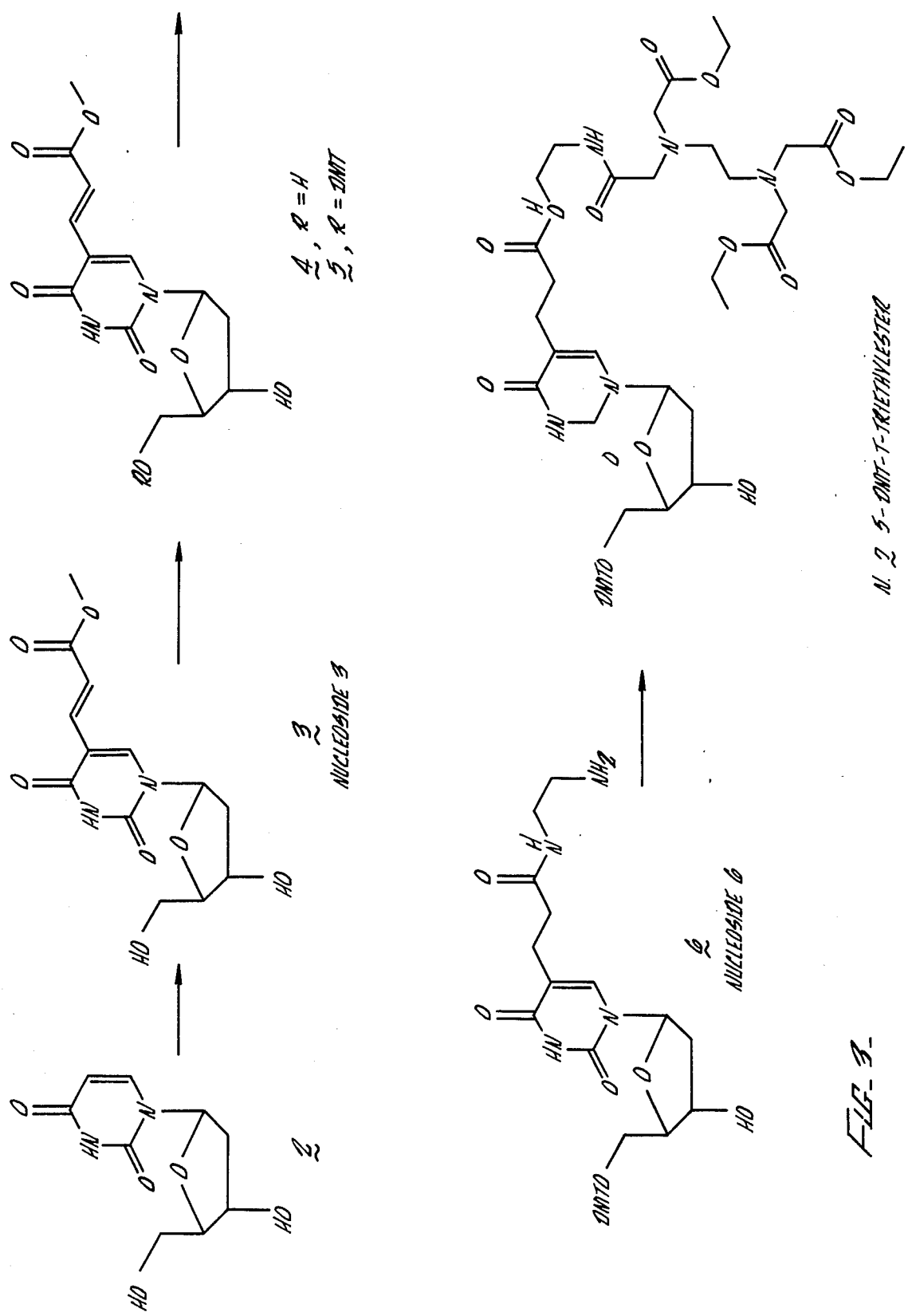
FIG. 3 is an autoradiogram showing the cleavage products of pBR322 DNA after exposure to the DNA-EDTA probe as analyzed by Maxam-Gilbert gel sequencing methods.

The products obtained by cleavage of the 167 bp restriction fragment of pBR322 are depicted in FIG. 3. Two cleavage sites of comparable intensity, nearly symmetrically distributed about the position of the probe (DNA-EDTA-Fe(II)) were observed on the labeled template strand (FIG. 3, lane 4).

A histogram of the DNA cleavage pattern obtained from densitometry of the autoradiogram is presented in FIG. 4. Each cleavage site covered 7-8 nucleotides, with maximum cleavage 4 nucleotides to the 5'-side and 3 nucleotides to the 3'-side of the probe. No observable cleavage of the labelled 167 bp template occurred under the reaction conditions if the DNA-EDTA probe was omitted (FIG. 3, lane 3) or if the template and probe were not heat denatured and hybridized prior to addition of Fe(II)/DTT. Furthermore, opposite-strand analysis showed no cleavage of the template strand containing the homologous sequence of the DNA-EDTA probe. Thus, when the reaction was repeated with the 167 bp template labeled with 32P on the 5'-end of the opposite strand, no cleavage was observed by autoradiography (FIG. 3, lane 5).

These results demonstrate that the DNA-EDTA probe, in the presence of Fe(II), dioxygen, and a reducing agent such as DTT, cleaves its complementary sequence in the heat-denatured 167 bp restriction fragment from pBR322. No other cleavage sites are observed. These results suggest that the probe forms a stable duplex with its complementary sequence, then chelates Fe(II) and in the presence of dioxygen $[O_2]$ effects localized DNA cleavage.

DNA-EDTA hybridized probe apparently forms an Fe(II) chelate which extends into the major groove of the right-handed DNA helix due to the site of attachment of the EDTA on the nucleoside.

This invention is not limited to chelator-probes constructed of DNA capable of sequence-specific cleavage of single-stranded DNA but can also be used to cause sequence-specific cleavage of RNA and denatured double-stranded DNA. Chelator-probes constructed of RNA may also be prepared utilizing sequences of ribonucleotides complementary to a given sequence of DNA or RNA.

The probes may also be labelled in various ways, for detection in diagnostic applications, for example with radioactive metals such as 99 mTc following the procedures of D. R. Elmalch et al., *Proc. Nat. Acad. Sci.* 81 p. 918 (1984) in EDTA, or with fluorescent elements such as the lanthamides Tb+3 or Eu+3. Charles S-H Leung et al, *Bioc. Biophys. Res. Comm.* 75, p. 15 (1977). As noted above, other metal chelators may be used in place of EDTA such as polyamines or other chelators capable of binding iron or copper. The metal ions used are also not limited to the Fe(II-III) in the demonstrated embodiment but may be any transition metal such as iron or Cu (I-II) that could participate in reducing dioxygen and oxidizing DNA. As discussed above, the metal chelator may be located at various positions within the polynucleotide sequence of the probe so long as it does not interfere with the ability of the polynucleotide to bind with its complementary DNA. In addition, more than one chelator-functionalized nucleoside may be incorporated per probe.

It is to be understood that various other modifications will be apparent to and can readily be made by those skilled in the art, given the disclosure herein, without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A polynucleotide probe for a specific nucleic acid sequence capable of cleaving said nucleic acid in the major groove, comprising:
   (a) a nucleotide sequence complementary to a specific single stranded nucleic acid sequence, said complementary nucleotide sequence containing at least one metal chelator; and
   (b) a metal ion bound to said metal chelator, said metal ion being capable of reducing dioxygen.

2. The polynucleotide probe according to claim 1 wherein said metal chelator is attached to a nucleoside of said nucleotide sequence by a tether.

3. The polynucleotide according to claim 2 wherein said tether is a hydrocarbon-polyamide linker.

4. The polynucleotide according to claim 3 wherein said tether is an ethylenediamine linker.

5. The polynucleotide probe according to claim 2 wherein said nucleoside to which the metal chelator is attached comprises a nucleoside base selected from the group of nucleoside bases consisting of cytosine, guanine, adenine, uracil and thymine.

6. The polynucleotide probe according to claim 2 wherein said nucleoside is the EDTA-functionalized nucleoside 5'-DMT-T*-triethylester.

7. The polynucleotide probe as recited in claim 1 wherein said metal chelator is a polyamino carboxylic acid metal chelator.

8. The polynucleotide probe according to claim 7 wherein said metal chelator is selected from the group consisting of EDTA, DCTA, DTPA, EDDHA or HEEDTA.

9. The polynucleotide probe according to claim 7 wherein said metal chelator is EDTA.

10. The polynucleotide probe according to claim 1 wherein said nucleotide sequence complementary to said specific nucleic acid sequence is comprised of deoxyribonucleotides.

11. The polynucleotide probe according to claim 1 wherein said nucleotide sequence complementary to said specific ribonucleic acid sequence is comprised of ribonucleotides.

12. The polynucleotide probe according to claim 1 wherein said specific nucleic acid sequence comprises single-stranded deoxyribonucleic acid.

13. The polynucleotide probe according to claim 1 wherein said specific nucleic acid sequence comprises ribonucleic acid.

14. The polynucleotide probe as recited in claim 1 wherein said metal ion is selected from the group consisting of iron and copper.

15. A polynucleotide probe for a specific single stranded nucleic acid sequence capable of cleaving said nucleic acid sequence at a specific site in the major groove, comprising:
(a) a nucleotide sequence complementary to said specified site, including at least one moleucle of EDTA connected to a nucleoside within said complementary nucleotide sequence by a tether; and
(b) at least one metal ion selected from the group consisting of iron and copper bound to said EDTA, said metal ion being capable of reducing dioxygen.

16. The polynucleotide probe as defined by claim 15 wherein said nucleoside is the EDTA-functionalized nucleoside 5'-"DMT-t*"triethylester.

17. The polynucleotide probe according to claim 15 wherein the nucleotide sequence is comprised of deoxyribonucleotides.

18. The polynucleotide probe according to claim 15 wherein the nucleotide sequence is comprised of ribonucleotides.

19. A polynucleotide probe for a specific ribonucleic acid sequence to be cleaved at a specific site in the major groove, comprising:
(a) a nucleotide sequence complementary to said specified site, including at least one moleucle of EDTA, connected to a nucleoside within said polynucleotide sequence by a tether; and
(b) at least one metal ion capable of reducing dioxygen selected from the group consisting of iorn and copper.

20. The polynucleotide probe according to claim 19 wherein said nucleoside is the EDTA-functionalized nucleoside 5'DMT-T*'triethylester.

21. The polynucleotide probe as defined by claim 19 wherein said nucleotide sequence is comprised of deoxyribonucleotides.

22. The polynucleotide probe as defined by claim 19 wherein said nucleotide sequence is comprised of ribonucleotides.

23. A process for cleaving nucleic acid in the major groove, comprising the steps of:
(a) hybridizing nucleic acid to be cleaved with a complementary sequence of polynucleotides containing at least one nucleoside to which is attached a metal chelator; and
(b) adding to said nucleic acid and complementary sequence of polynucleotides a metal ion capable of binding to said chelator, said metal ion being capable of reducing dioxygen; and
(c) cleaving said nucleic acid.

24. The process of claim 23 wherein said metal chelator is EDTA.

25. The process of claim 23 wherein said nucleic acid is deoxyribonucleic acid.

26. The process of claim 23 wherein said nucleic acid is ribonucleic acid.

27. The process for cleaving nucleic acid as recited in claim 23 which includes the step of adding dithiothreitol.

28. The process for cleaving nucleic acid as recited in claim 23 wherein said nucleic acid is single-stranded deoxyribonucleic acid.

29. The process for cleaving nucleic acid according to claim 23 wherein said nucleic acid is ribonucleic acid.

30. A process for identifying the presence of a selected single stranded nucleic acid sequence comprising the steps of:
(a) hybridizing said selected nucleic acid sequence with a polynucleotide probe, said probe comprising a nucleotide sequence complementary with at least a portion of said selected nucleic acid sequence and containing at least one metal chelator attached to a nucleoside within said complementary nucleotide sequence by a tether;
(b) adding at least one detectable metal ion capable of binding to said metal chelator, said metal ion being capable of reducing dioxygen; and
(c) detecting the presence of said detectable metal ion within the major groove thereby locating said nucleic acid sequence.

31. The process of claim 30 wherein said nucleic acid sequence comprises deoxyribonucleic acid.

32. The process of claim 30 wherein said nucleic acid sequence is ribonucleic acid.

33. A process for identifying the presence of a nucleic acid sequence as recited in claim 30 wherein said metal ion fluoresces.

34. A process for identifying the presence of a nucleic acid sequence as recited in claim 30 wherein said metal ion is radioactive.

35. A process for identifying the presence of a nucleic acid sequence as recited in claim 30, wherein said nucleic acid codes for a virus.

36. A process for identifying the presence of a nucleic acid sequence as recited in claim 30 wherein said nucleic acid codes for an oncogene.

37. The process for identifying the presence of a nucleic acid as recited in claim 30 wherein said nucleic acid is single-stranded deoxyribonucleic acid.

38. A polynucleotide hybridization probe incorporating at least one nucleoside functionalized by tethering to a metal cheloatr for cleaving a substantailly complementary nucleotide strand such that clevage occurs in the major groove, said metal chelator having bound thereto a metal ion capable of reducing dioxygen.

39. A process for synthesizing a polynucleotide hybridization probe for cleaving a substantailly complementary nucleotide strand such that said cleavage occurs in the major groove, comprising:
(a) functionalizing at least one nucleoside by tethering to a metal chelators;
(b) incorporating said functionalized nucleosides into polynucleotide sequences substantially complementary to specific nucleotide sequences to be cleaved; and
(c) chelating to said metal chelators metal ions capable of reducing dioxygen.

* * * * *